United States Patent [19]

Robach

[11] 4,400,403

[45] Aug. 23, 1983

[54] PRESERVATION WITH ACYLOXY-5-HEXENOIC AND ACYLOXY-4-HEXENOIC ACIDS

[75] Inventor: Michael C. Robach, St. Peters, Mo.

[73] Assignee: Monsanto Company, St. Louis, Mo.

[21] Appl. No.: 256,323

[22] Filed: Apr. 22, 1981

[51] Int. Cl.$^3$ .................... A23L 3/24; A01N 37/06
[52] U.S. Cl. .................. 426/532; 426/335; 424/311; 424/312; 424/314
[58] Field of Search .............. 426/532, 335; 424/311, 424/312, 314

[56] References Cited

U.S. PATENT DOCUMENTS 2,379,294  6/1945  Gooding .......................... 424/314
2,997,394  8/1961  Melnick et al. ................. 426/532 X

*Primary Examiner*—Joseph M. Golian
*Attorney, Agent, or Firm*—G. R. Beck; R. E. Wexler

[57] ABSTRACT

The storage life of foods and feeds is extended by treating same with acyloxyalkenoic acids, especially a mixture of acetoxyhexenoic acids. The acyloxyalkenoic acids are shown to inhibit pathogens and food spoilage organisms in laboratory culture media and foodstuffs.

13 Claims, No Drawings

PRESERVATION WITH ACYLOXY-5-HEXENOIC AND ACYLOXY-4-HEXENOIC ACIDS

BACKGROUND OF THE INVENTION

This invention relates to a novel compound for increasing the storage life of food and feed products which normally spoil or lose flavor. Additionally, this invention relates to a method for increasing the storage life of such food and feed products and to food and feed product compositions containing such compounds. In particular, this invention is related to inhibiting the growth of pathogens and food spoilage organisms in food and feed products which normally spoil or lose flavor during storage.

Deterioration due to pathogenic and spoilage organisms occurs extensively in untreated foodstuffs such as bakery products, fish, meats, fruits, vegetables and dairy products. Industrial food processing plants incur losses both in the form of returned, deteriorated products and of impaired sales owing to inferior keeping quality of the products. Consumers, also, are caused direct losses by such deterioration but, in addition, they also run health risks because of the toxins formed by pathogens which may already be produced before the growth of such pathogens is observable. Heretofore, attempts have been made to prevent or inhibit the growth of microorganisms such as pathogens and food spoilage organisms by using packaging materials which have been treated by a variety of substances and by intensifying plant hygiene and thus reducing the amount of pathogenic and food spoilage organism infection. Intensified food plant hygiene has successfully lowered the frequency of pathogenic and food spoilage organisms to a significant degree, however it is impossible, in practice, to solve the problem completely by this approach, since it has not been possible to reduce to a sufficiently low level the organism infection by which food is contaminated even by such expedients as filtration of intake air and ultraviolet light treatment.

Aerobic microorganisms are deposited on the surface of food or feed through post-processing contamination from the air, from the hands of an operator, from equipment and utensils and other means. Typical examples are the formation of slime on the surfaces of slaughtered animal carcasses, or the growth of bacterial colonies on sliced sausages.

Since post-processing microbial contamination, in most cases, remains on the surface of the food or feed, aerobic microorganisms generally can multiply only on the superficial layers of the food or feed. Accordingly, the measures aimed at fighting such microorganisms are concentrated on the superficial layer and the desired preventative effect can thereby be achieved. The procedures applied heretofore for the purpose of applying chemical or equivalent inhibitors of microorganism growth on the superficial layer of food or feed products have been dipping the food in a solution of chemical preservative, spraying a chemical preservative solution onto the surface of food or feed and impregnating packaging material with a chemical preservative. A wide variety of such chemical preservatives have heretofore been used.

For instance, U.S. Pat. No. 2,711,976 suggests the use of amino acids to increase the resistance of custard foods to spoilage organisms and *Staphylococcus aureus*. U.S. Pat. No. 2,898,372 suggests calcium acetate propionate as a bread treating composition. U.S. Pat. No. 2,866,819 suggests the use of sorbic acid as a preservative in foods. U.S. Pat. No. 2,910,368 discloses the use of EDTA with sorbic acid to increase the shelf life of vegetables. U.S. Pat. No. 2,992,114 suggests the use of sorbic acid and a mild heat treatment for the preservation of fruits and vegetables. In a paper published in *Applied Microbiology*, Volume 18, pages 68–75 (July, 1969), Preonas et al reported on the use of a mixture of sorbic acid and propionic acid to retard the growth of *S. aureus* on the surfaces of custard pies.

In copending application Ser. No. 222,200 filed Jan. 2, 1981 now U.S. Pat. No. 4,356,317 and assigned to the present assignee, there are described acyloxyalkenoic acids which are characterized as hexenoic acids having up to one alkyl substituent on the alpha carbon atom and an acyloxy substituent on a carbon atom, the acyloxy substituent being represented by RCOO—, where R is alkyl, and their salts. In particular, there are described such compounds in which acyloxy is acetoxy, and, more particularly, a mixture of isomeric acids which are 6-acyloxy-4-hexenoic and 4-acyl-oxy-5-hexenoic acids and their salts.

In accordance with the present invention, there is described and claimed a method of inhibiting the growth of pathogens and spoilage organisms in foods and feeds by treating same with acyloxyhexenoic acids and there are described and claimed food and feed compositions containing such acids.

SUMMARY OF THE INVENTION

The present invention describes the use of acyloxyhexenoic acids and their salts to inhibit the growth of pathogens and food spoilage organisms in foods and feeds.

The present invention is further concerned with extending the useful storage life of food and feed products which are susceptible to contamination and spoilage.

The present invention comprises broadly suppressing common food and feed product pathogens and common spoilage organisms in food and feed products which render such products unpalatable or unsafe to eat after a finite period of time.

The means for accomplishing the purpose of this invention comprises treating the food and feed products with an acyloxyhexenoic acid per se or in a diluent therefor. Especially preferred acyloxyhexenoic acids are 4-acetoxy-5-hexenoic acid and 6-acetoxy-4-hexenoic acid which, in an isomeric ratio of 56% of the former with 44% of the latter, comprises a mixture identified broadly as acetoxy acid (AA). Other members of this family of acids which would be expected to inhibit the growth of microorganisms in the same fashion as acetoxy acid are acyloxyhexenoic acids which are hexenoic acids having up to one alkyl or alkenyl substituent on the alpha carbon atom and an acyloxy substituent on one carbon atom, said acyloxy substituent being represented by RCOO— wherein R is alkyl or alkenyl, and their salts.

Thus, the isomeric acyloxyalkenoic acids are represented by the structures

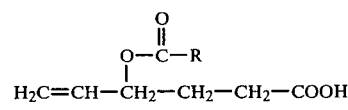

or

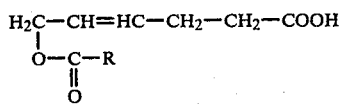

wherein an alkyl or alkenyl substituent, $R_1$, may replace a hydrogen atom on the alpha carbon atom. The sum of R and $R_1$ should not exceed 19 carbon atoms in order to avoid solubility problems. Accordingly, either R or $R_1$ may represent alkyl or alkenyl having up to 19 carbon atoms. Thus R and $R_1$ may represent alkyl, e.g. methyl, ethyl, propyl, butyl, amyl, hexyl, heptyl, actyl, nonyl, decyl, undecyl, dodecyl, tridecyl, quaterdecyl, pentadecyl, hexadecyl, heptadecyl, octadecyl, nonadecyl. Also, R and $R_1$ may represent ethylene, propylene, butylene, amylene, hexylene, heptylene, octylene, nonene, decene, undecene, dodecene, tridecene, quaterdecene, pentadecene, hexadecene, heptadecene, octadecene, nonadecene. The alkyl and alkenyl substituents which are represented by R and $R_1$ may be straight or branched chain and may themselves contain substituents which are not inconsistent with the preservative action of the compounds and their intended use in foods and feeds. As stated supra, the sum of R and $R_1$ should not exceed 19 carbon atoms. Thus, if R is 10 carbon atoms, $R_1$ should not exceed 9 carbon atoms. Similarly if $R_1$ is not present, R may be up to 19 carbon atoms.

While the exemplification of the invention of most immediate interest involves reaction of acetic acid with butadiene to obtain acetoxyhexenoic acids, the invention also includes use of other acids in place of acetic acid. Other acids having at least one replaceable hydrogen atom on the alpha carbon atom react similarly to acetic acid, particularly lower alkanoic acids, such as propionic, butyric, hexanoic acids, etc. Useful acids can be represented by the formula $RCH_2CO_2H$ or $R_2CHCO_2H$, where R is hydrogen or a monovalent organic group, preferably an alkyl group having, for example, 1 to 4 carbon atoms.

Such acids can be oxidized to radicals, $-CHRCO_2H$, e.g., carboxyalkane radicals, and react with butadiene to produce substituted acyloxyhexenoic acids, $RCH_2COOCH_2CH=CHCH_2CHR-COOH$, and

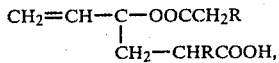

for example 6-acyloxy-2-alkyl-4-hexenoic acids and 4-acyloxy-2-alkyl-5-hexenoic acids. In the event that acids other than acetic are reacted, but acetic acid is also present as solvent, or metal salt, a mixed product may be obtained, depending upon the relative activities of the acids toward the reaction. Thus in the products represented by the above formula, in some cases R would by hydrogen where the reactant was from acetic acid and in other cases R would be a group from another acid, such as a methyl group from propionic acid.

The salts of the contemplated compounds may also be used in the process of this invention. Thus, there may be used the alkali metal, alkaline earth metal and ammonium salts of such compounds, e.g. Na, K, Ca, Mg and $NH_4$ salt.

Application of the acyloxyhexenoic acid to the food or feed product is by dipping or otherwise immersing the food or feed product in the acid or by spraying the acid, either in concentrated form or in a diluent therefor, onto the feed or food product.

Among the microorganisms of which the acyloxyhexenoic acids have been found to be effective as growth inhibitors are the nonlactic acid gram positive bacteria such as *S. aureus, Bacillus cereus, Clostridium perfringens* and other clostridial species and the Micrococcus species. Additionally, the acyloxyhexenoic acids have been found to be effective growth inhibitors of gram negative bacteria such as Salmonella species, *Escherichia coli, Vibrio parahemolyticus* and species of Pseudomonas, Alcaligines and Flavobacterium. Furthermore, the acyloxyhexenoic acids have been found to be a growth inhibitor, although to a lesser extent than with microorganisms, against yeasts such as *Candida albicans, Saccharomyces cerevisiae* and against molds such as Aspergillus, *Penicillium italicum* and *Fusarium roseum*, particularly at low pH. Among the food products which are particularly benefited by treatment with acyloxyhexenoic acids are foods which have high water activity and which are subject to temperature abuse, i.e. improper storage and transportation temperature conditions, such as packaged meat products, dairy products, prepared salad products and prepared entree products of all types.

Among feed products which are benefited by treatment with acyloxyhexenoic acids are those byproduct feeds which are subject to pathogen attack, e.g. fishmeal, poultry byproduct meal and rendered animal wastes.

The concentration of acyloxyhexenoic acid compound which is effective in the method of this invention is generally in the range of from about 0.005% to about 0.5%, more particularly from about 0.05% to about 0.3% and, especially, from about 0.1% to about 0.2%. The specific concentration of acid with which a particular food or feed product is treated will vary, depending upon the specific food, its water content, the intended environment of storage and length of time thereof, contamination level and the presence of other preservative agents.

EXAMPLES OF PREFERRED EMBODIMENTS

In Tables I, II and III acetoxy acids were tested for antimicrobial activity against certain food poisoning bacteria. The acetoxy acids employed were a purified mixture of 6-acetoxy-4-hexenoic acid and 4-acetoxy-5-hexenoic acid produced by reaction of butadiene with acetic acid and anhydride in the presence of manganese salts. The tests were conducted utilizing trypticase soy broth. The growth of specified bacteria was monitored using standard plate count methods daily for three days. The results are reported below in Table I in the log of the number of cells per ml. The values are approximate, having been transposed from graphic form.

TABLE I

| | Log No. Cells/ml | | | | | | | |
|---|---|---|---|---|---|---|---|---|
| | Staphylococcus Aureus S-6 | | | | Staphylococcus Aureus 12000 | | | |
| | pH 6 | | pH 6.5 | | pH 6 | | pH 6.5 | |
| Additive | 1 day | 3 days | 1 day | 3 days | 1 day | 3 days | 1 day | 3 days |
| Control | 5.7 | 9.2 | 8.8 | 9.0 | 8.5 | 9.1 | 8.8 | 9.1 |
| 0.1% sorbate | 5.4 | 9.0 | 8.5 | 8.8 | 5.5 | 8.8 | 8.5 | 8.9 |
| 0.2% sorbate | 4.4 | 8.8 | 8.3 | 8.4 | 3.5 | 8.3 | 8.4 | 8.5 |
| 0.1% AA | 3.9 | 9.1 | 6.7 | 8.7 | 3.7 | 8.6 | 3.6 | 8.8 |
| 0.2% AA | 3.6 | 4.8 | 3.5 | 3.8 | 2.8 | 5.7 | 2.5 | 4.0 |

*Staphylococcus aureus* FDA 743 was inoculated into trypticase soy broth and incubated at 30° C. for 24 hours. The bacterium was then inoculated into tubes of the broth of specified pH and preservative combination and incubated at 30° C. The acetoxyhexenoic acids used were comparable to those used above. The optical density at a 600 nanometer setting was then read periodically. The qualitative degree of inhibition, and six-day end points are reported in Table II below.

TABLE II

|  | pH 8 | | pH 7 | | pH 6 | |
| --- | --- | --- | --- | --- | --- | --- |
|  | Inhibition | End Point (O.D.) | Inhibition | End Point (O.D.) | Inhibition | End Point (O.D.) |
| Control | — | 0.4 | — | 0.6 | — | 0.6 |
| 0.2% K sorbate | None | 0.4 | None | 0.6 | — | — |
| 0.2% acetoxy acid | None | 0.5 | Virtually Complete | 0 | — | — |
| 0.05% K sorbate | — | — | — | — | Slight | 0.6 |
| 0.10% K sorbate | — | — | — | — | Slight | 0.6 |
| 0.05% acetoxy acid | — | — | — | — | Moderate* | 0.6 |
| 0.10% acetoxy acid | — | — | — | — | Complete | 0 |

*Initial growth delayed for three days.

It can be seen that the acetoxyhexenoic acids were very effective inhibitors at pH's 6 and 7. At a 15° C. incubation temperature, the effect of the agents against *S. aureus* was pH dependent but with the acetoxyhexenoic acids having a broader range of effectiveness than the sorbate, with both potassium sorbate and acetoxy acids at 0.2% concentration showing no effect at pH 8, with the sorbate showing little or no effect at pH 7, while the acetoxy acids gave virtually complete inhibition at pH 6.

Effectiveness against *Clostridium perfringens* was tested in trypticase soy broth at 30° C. by the above procedure and results obtained as reported below in Table III.

TABLE III

|  | pH 8 | pH 7 | | pH 6 | | pH 5.5 | |
| --- | --- | --- | --- | --- | --- | --- | --- |
|  | End Point (O.D.) | Inhibition | End Point (O.D.) | Inhibition | End Point (O.D.) | Inhibition | End Point (O.D.) |
| Control | 0.7 | — | 0.5 | — | 1.1 | — | 0.6 |
| 0.2% K sorbate | 0.6 | None | 0.6 | — | — | — | — |
| 0.2% acetoxy acid | 0.5 | Complete | 0 | — | — | — | — |
| 0.05% K sorbate | — | — | — | Moderate | 0.4 | Strong | 0 |
| 0.1% K sorbate | — | — | — | Moderate | 0.2 | Complete | 0 |
| 0.05% acetoxy acid | — | — | — | Moderate | 0.4 | None | 0.6 |
| 0.1% acetoxy acid | — | — | — | Moderate* | 0.2 | Moderate | 0.2 |

*Delayed onset of growth 2 days.

It is notable that at pH 7 the acetoxy acids were completely inhibitory, while the sorbate was ineffective. At a 15° incubation temperature, 0.2% amounts of the sorbate and acetoxy acids were slightly effective at pH 8.0 against *C. perfringens* with the sorbate being somewhat the better, while at pH 7.0 the sorbate was only slightly effective while the acetoxy acids gave complete inhibition. At pH 6.0, neither was effective at 0.05% amounts, while both gave virtually complete inhibition at 0.1%.

At 30° C. 0.2% of acetoxy acids completely inhibits growth of *Bacillus cereus* in pH 8.0 broth compared to no effect for sorbate, but only slightly reduces growth at pH 7.0; at pH 6.0, 0.1% is very inhibitory while 0.1% sorbate is only slightly inhibitory. No growth occurred below pH 6.0. At 15° C., 0.2% acetoxy acid was almost completely inhibitory at pH 8.0 and pH 7.0, being much better than sorbate which was only slightly inhibitory; at pH 6.0 and below no growth occurred in the presence of the preservatives.

It can be concluded that acetoxyhexenoic acids possess strong antimicrobial activity against gram positive bacteria which is generally greater than that of sorbic acid, and that the activity generally extends up to pH 7, and in some cases higher. This is significant as many foods to be preserved have pH's in the range of 5 to 6.5, and the acetoxyhexenoic acids appear more than sufficiently inhibitory in such ranges.

In the antimicrobial comparisons herein, sorbic acid is generally used in the form of its potassium salt in order to have water solubility because of the aqueous broth employed in the tests, while the acetoxyhexenoic acids can be used in acid form as the solubility is sufficient.

The acetoxyhexenoic acids were generally not as effective against yeasts and molds as sorbic acid, although acetoxyhexenoic acid at 0.2% was somewhat more effective than sorbate at 15° against *C. albicans*, and was effective to some extent against *Penicillium italicum* and *Fusarium roseum* at low pH's.

Against Salmonella at 30° C. a 0.20% acetoxy acid was very slightly effective at pH 8.0, moderately effective at pH 7.0, and strongly effective at pH 6.0. The compound was moderately to slightly effective at pH's 5.5 and 5.0, with a 0.10% concentration being better than 0.20%. Potassium sorbate gave similar results at pH 6.0 but better results at pH 5.5 and pH 5.0, although the acetoxy acids delayed onset of growth at pH's 6.0 and 5.5.

At 15° C., acetoxy acids gave some inhibition of growth of Salmonella in 7-day tests over pH's from 8.0 to 5.5, and delayed onset of growth compared to potassium sorbate, although later growth was rapid. At pH 6.0 a 0.2% concentration of acetoxy acids was seriously inhibitory over the 7-day tests, as was 0.10% acetoxy acid at pH 5.5.

With regard to gram negative bacteria, results indicate that in general acetoxy acid and potassium sorbate are comparable in effect against growth of the bacteria, with the acetoxy acid generally being more effective above pH 6.0, while the sorbate is generally more effective as the pH drops.

The acyloxyhexenoic acids in general as described herein are expected to exhibit antimicrobial properties similar to those of the 6- and 4-acetoxy-hexenoic acids used as exemplifications herein.

Table IV exhibits the preservative action of acetoxy acid when used in cottage cheese and tuna salad stored at 10° C. The cottage cheese and tuna salad were placed in petri dishes and stored at 10° C. Samples were analyzed for total plate count after 2, 4 and 6 days of storage.

In Table IV the data regarding cottage cheese indicate that 0.05% acetoxy acid allowed only a 1.5 log cycle increase of bacteria whereas the control product has a population increase of 2.5 log cycles.

The data regarding tuna salad in Table IV indicate that the use of 0.10% acid resulted in about a one log cycle decrease in final population as compared to the control product.

TABLE IV

| | Log No. Cells/g. Total Microorganism Plate Count | | | |
|---|---|---|---|---|
| | Cottage Cheese | | | |
| Additive | pH 5.3 0 Days | 2 Days | 4 Days | pH 5.4 6 Days |
| Control | 4.2 | 5.7 | 6.8 | 6.7 |
| 0.05% AA | 4.3 | 5.2 | 5.3 | 5.8 |
| | Tuna Salad | | | |
| | pH 5.3 0 Days | 2 Days | 4 Days | pH 5.3 6 Days |
| Control | 4.0 | 5.3 | 6.1 | 6.3 |
| 0.10% AA | 4.0 | 4.2 | 5.1 | 5.5 |

In general, the above data indicate that acetoxy acid is not as effective against yeasts and molds as is sorbic acid and that acetoxy acid is more effective against pathogens and spoilage bacteria at higher pH than is sorbic acid, whereas sorbic acid is more effective at lower pH.

Accordingly, it is contemplated that a composition comprising acetoxy acid and sorbic acid or their salts would have an overall greater effectiveness over a wider pH range than either preservative would have by itself. Such composition would contain sorbic acid or its salts at a concentration of from about 0.025 to about 0.1% by weight. The ratio of acetoxy acid to sorbic acid would vary from about 2:1 to 1:2, preferably about 1:1.

In view of the present disclosure, it is contemplated that acetoxy acids, other than the specific acetoxy acid utilized in the examples, would function similarly. Accordingly, it is contemplated that the salts of the acids, as described above, would show similar effectiveness as would other species of acid within the general genus of acids described.

I claim:

1. A method of inhibiting growth of pathogenic or food spoilage microorganisms which comprises contacting same with an effective growth inhibiting amount of acyloxyhexenoic acid selected from acyloxy-5-hexenoic acid and acyloxy-4-hexenoic acid, mixtures thereof, salts thereof and mixtures of said salts, said acyloxyhexenoic acid having up to one $R_1$ substituent on the alpha carbon atom, said acyloxy being represented by RC00-, and said R and $R_1$ being alkyl or alkenyl having a total of up to 19 carbon atoms.

2. Method of claim 1 wherein said acid is selected from 6-acetoxy-4-hexenoic acid and 4-acetoxy-5-hexenoic acid and salts thereof, mixtures of said acids and mixtures of said salts.

3. A method of inhibiting growth of pathogenic or food spoilage microorganism in a food or feed product which comprises treating said product with an effective growth inhibiting amount of acyloxyhexenoic acid selected from acyloxy-5-hexenoic acid and acyloxy-4-hexenoic acid, mixtures thereof, salts thereof and mixtures of said salts, said acyloxyhexenoic acid having up to one $R_1$ substituent on the alpha carbon atom, said acyloxy being represented by RC00-, and said R and $R_1$ being alkyl or alkenyl having a total of up to 19 carbon atoms.

4. Method of claim 1 wherein said acid is selected from 6-acetoxy-4-hexenoic acid and 4-acetoxy-5-hexenoic acid and salts thereof, mixtures of said acids and mixtures of said salts.

5. A composition comprising a food or feed product and an effective pathogenic or food spoilage microorganism growth inhibiting amount of acyloxyhexenoic acid selected from acyloxy-5-hexenoic acid and acyloxy-4-hexenoic acid, mixtures thereof, salts thereof and mixtures of said salts, said acyloxyhexenoic acid having up to one $R_1$ substituent on the alpha carbon atom, said acyloxy being represented by RC00-, and said R and $R_1$ being alkyl or alkenyl having a total of up to 19 carbon atoms.

6. Composition of claim 5 wherein said acid is selected from 6-acetoxy-4-hexenoic acid and 4-acetoxy-5-hexenoic acid and salts thereof, mixtures of said acids and mixtures of said salts.

7. Composition of claim 6 wherein said acid is a mixture of 6-acetoxy-4-hexenoic acid and 4-acetoxy-5-hexenoic acid and salts thereof.

8. A method of inhibiting growth of pathogenic or food spoilage microorganisms which comprises contacting same with an effective growth inhibiting amount of a mixtures of sorbic acid and acyloxyhexenoic acid selected from acyloxy-5-hexenoic acid and acyloxy-4-hexenoic acid, mixtures thereof, salts thereof and mixtures of said salts, said acyloxyhexenoic acid having up to one $R_1$ substituent on the alpha carbon atom, said acyloxy being represented by RC00-, and said R and $R_1$ being alkyl or alkenyl having a total of up to 19 carbon atoms and wherein the ratio of acylohexenoic acid to sorbic acid varies from about 2:1 to 1:2.

9. Method of claim 8 wherein said acyloxyhexenoic acid is a mixture of 6-acetoxy-4-hexenoic acid and 4-acetoxy-5-hexenoic acid and salts thereof.

10. A composition comprising a mixture of sorbic acid and acyloxyhexenoic acid selected from acyloxy-5-hexenoic acid and acyloxy-4-hexenoic acid, mixtures thereof, salts thereof and mixtures of said salts, said acyloxyhexenoic acid having up to one $R_1$ substituent on the alpha carbon atom, said acyloxy being represented by RC00-, and said R and $R_1$ being alkyl or alkenyl having a total of up to 19 carbon atoms and wherein the ratio of acylohexenoic acid to sorbic acid varies from about 2:1 to 1:2.

11. Composition of claim 10 wherein said acyloxyhexenoic acid is a mixture of 6-acetoxy-4-hexenoic acid and 4-acetoxy-5-hexenoic acid.

12. A composition comprising a food or feed product and a pathogenic or food spoilage microorganism growth inhibiting amount of a composition of claim 10.

13. Composition of claim 12 wherein said acyloxyhexenoic acetoxy acid is a mixture of 6-acetoxy-4-hexenoic acid and 4-acetoxy-5-hexenoic acid and salts thereof.

* * * * *

UNITED STATES PATENT AND TRADEMARK OFFICE
CERTIFICATE OF CORRECTION

PATENT NO. : 4,400,403
DATED : August 23, 1983
INVENTOR(S) : Michael C. Robach

It is certified that error appears in the above-identified patent and that said Letters Patent is hereby corrected as shown below:

Column 8, Claim 4, line 1, "1" should be --- 3 ---.

Column 8, Claim 8, line 4, "mixtures" should be --- mixture ---.

Column 8, Claim 13, line 2, "acetoxy" should be deleted.

Signed and Sealed this

Fifteenth Day of November 1983

[SEAL]

Attest:

Attesting Officer

GERALD J. MOSSINGHOFF

Commissioner of Patents and Trademarks